(12) United States Patent
Erickson et al.

(10) Patent No.: US 8,672,972 B2
(45) Date of Patent: Mar. 18, 2014

(54) LOW PROFILE VERTEBRAL STABILZATION SYSTEMS AND METHODS

(75) Inventors: David R. Erickson, Memphis, TN (US); Troy D. Drewey, Memphis, TN (US); Robert A. Farris, Cordova, TN (US); Jason Michael May, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 151 days.

(21) Appl. No.: 13/183,110

(22) Filed: Jul. 14, 2011

(65) Prior Publication Data

US 2011/0276096 A1    Nov. 10, 2011

Related U.S. Application Data

(62) Division of application No. 11/524,804, filed on Sep. 21, 2006, now Pat. No. 7,988,711.

(51) Int. Cl.
*A61B 17/70* (2006.01)

(52) U.S. Cl.
USPC .......................................................... 606/246

(58) Field of Classification Search
USPC ..................... 606/246–279; 403/270; 411/82
See application file for complete search history.

(56) References Cited

U.S. PATENT DOCUMENTS

| | | |
|---|---|---|
| 5,534,001 A | 7/1996 | Schlapfer et al. |
| 5,550,172 A | 8/1996 | Regula et al. |
| 5,702,395 A | 12/1997 | Hopf |
| 5,814,046 A | 9/1998 | Hopf |
| 5,989,250 A | 11/1999 | Wagner et al. |
| 6,090,111 A | 7/2000 | Nichols |
| 6,296,643 B1 | 10/2001 | Hopf et al. |
| 6,299,613 B1 | 10/2001 | Ogilvie et al. |
| 6,416,515 B1 | 7/2002 | Wagner |
| 6,524,315 B1 | 2/2003 | Selvitelli et al. |
| 6,565,565 B1 | 5/2003 | Yuan et al. |
| 6,607,530 B1 | 8/2003 | Carl et al. |
| 6,610,063 B2 | 8/2003 | Kumar et al. |
| 6,613,050 B1 | 9/2003 | Wagner et al. |
| 6,616,669 B2 | 9/2003 | Ogilvie et al. |
| 6,652,587 B2 * | 11/2003 | Felt et al. ................... 623/20.16 |
| 6,706,044 B2 | 3/2004 | Kuslich et al. |
| 6,723,095 B2 | 4/2004 | Hammerslag |
| 6,755,829 B1 | 6/2004 | Bono et al. |
| 6,786,903 B2 | 9/2004 | Lin |
| 6,923,811 B1 | 8/2005 | Carl et al. |
| 6,979,333 B2 | 12/2005 | Hammerslag |
| 7,041,103 B2 | 5/2006 | Hoffmann-Clair et al. |
| 7,066,938 B2 | 6/2006 | Slivka et al. |
| 7,081,117 B2 | 7/2006 | Bono et al. |

(Continued)

OTHER PUBLICATIONS

Trigon Research Studies, How it works: The Viazi Bracket, http://www.viazissystem.com/seehow.asp, 3 pgs., date unknown.

(Continued)

*Primary Examiner* — Eduardo C Robert
*Assistant Examiner* — Steven Cotroneo (57) ABSTRACT

Skeletal stabilization systems include a base, a longitudinal member, and a retaining member. The base includes an engagement surface with a surface area that is positionable in contact with a bone to atraumatically or traumatically engage the base to the bone. The retaining member engages the base to retain the longitudinal member relative to the base so that the longitudinal member can provide a desired stabilization effect to one or more adjacent bony portions.

19 Claims, 9 Drawing Sheets

(56) References Cited

U.S. PATENT DOCUMENTS

| | | |
|---|---|---|
| 7,118,571 B2 | 10/2006 | Kumar et al. |
| 7,141,051 B2 | 11/2006 | Janowski et al. |
| 7,235,075 B1 | 6/2007 | Metz-Stavenhagen |
| 7,320,556 B2 | 1/2008 | Vagn-Erik |
| 2002/0120272 A1 | 8/2002 | Yuan et al. |
| 2003/0125737 A1 | 7/2003 | Hammerslag |
| 2003/0125742 A1 | 7/2003 | Yuan et al. |
| 2003/0135209 A1 | 7/2003 | Seedhom et al. |
| 2003/0191468 A1 | 10/2003 | Hoffman et al. |
| 2003/0224317 A1 | 12/2003 | Andreiko et al. |
| 2004/0059333 A1 | 3/2004 | Carl et al. |
| 2004/0236330 A1* | 11/2004 | Purcell et al. .................. 606/61 |
| 2004/0249376 A1 | 12/2004 | Hammerslag |
| 2005/0131406 A1* | 6/2005 | Reiley et al. .................. 606/61 |
| 2005/0228378 A1 | 10/2005 | Kalfas et al. |
| 2005/0267481 A1 | 12/2005 | Carl et al. |
| 2005/0288671 A1 | 12/2005 | Yuan et al. |
| 2006/0095036 A1 | 5/2006 | Hammerslag |
| 2006/0155278 A1* | 7/2006 | Warnick .................. 606/61 |
| 2006/0167453 A1 | 7/2006 | Hoffman-Clair et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0235391 A1* | 10/2006 | Sutterlin .................. 606/61 |
| 2006/0235393 A1 | 10/2006 | Bono et al. |
| 2006/0247636 A1 | 11/2006 | Yuan et al. |
| 2007/0043357 A1* | 2/2007 | Kirschman .................. 606/61 |
| 2007/0055242 A1 | 3/2007 | Bailly |
| 2007/0055243 A1 | 3/2007 | Kumar et al. |
| 2007/0093827 A1 | 4/2007 | Warnick |
| 2007/0123862 A1 | 5/2007 | Warnick |
| 2007/0123867 A1 | 5/2007 | Kirschman |
| 2007/0167948 A1* | 7/2007 | Abdou .................. 606/61 |
| 2008/0051788 A1 | 2/2008 | Schwab |
| 2008/0071277 A1 | 3/2008 | Warnick |

OTHER PUBLICATIONS

3M Unitek, SmartClip Self-Ligating Appliance System, Excellence Has Evolved, Copyright 2006, 9 pgs., Monrovia, California.

iBraces—Invisible Braces that Work for You, http://www.lingualcare.com/doctor/info.htm, 2 pgs., date unknown.

Damon System, Damon3, http://www.ormco.com/index/damon-thesystem-damon3-thebracket-01, 2 pgs., date unknown.

Blugloo Two-Way Color Change Adhesive, For Aesthetic Brackets, Technique Guide, 3 pgs., SDS Ormco, Glendora, California, date unknown.

In-Ovation, The World's Only Twin With The Active Clip, The Future of Orthodontics From GAC, 12 pgs., GAC International, Inc., Bohema, New York, date unklnmown.

The Shape of Comfort, Opal-M, 12 pgs., Opal Orthodontics, Ultradent Products USA, Berg, Germany, date unknown.

* cited by examiner

Fig. 11A    Fig. 11B

LOW PROFILE VERTEBRAL STABILZATION SYSTEMS AND METHODS

REFERENCE TO RELATED APPLICATIONS

This application is a divisional of co-pending U.S. patent application Ser. No. 11/524,804 filed Sep. 21, 2006, the contents of which are hereby incorporated by reference in their entirety.

BACKGROUND

In certain vertebral stabilization systems it is desired to secure a longitudinal member along one or more vertebral levels of the spinal column to provide stabilization to the vertebrae. Fasteners that secure the longitudinal member to the vertebrae can require significant alteration of the bone. The fasteners can also project from the bone into the adjacent tissue in order to accommodate the components of the fastener and the longitudinal member. Fasteners can also require the handling and placement of multiple small components to engage the longitudinal member to the fasteners. While various vertebral and skeletal stabilization systems have been developed, a need remains for low profile stabilization systems that facilitate and expedite engagement to the bone and engagement of the longitudinal member along the bone.

SUMMARY

The present invention relates to skeletal stabilization systems, and more particularly, but not exclusively, relates to vertebral stabilization systems having a coupling member securable to a vertebral body and a longitudinal member engaged to the coupling member. Multiple coupling members may be employed and secured along the longitudinal member to multiple vertebrae to stabilize one or more vertebral levels. The longitudinal member may be employed alone or in combination with one or more other longitudinal members along the same or different levels of the spinal column.

One embodiment includes a vertebral stabilization system having a coupling member securable to a vertebral body. The coupling member includes a base and a retaining member securable to the base to couple a longitudinal member positioned along the spinal column to the coupling member. In one embodiment, the coupling member includes an engagement surface with an adhesive to atraumatically engage the coupling member to a vertebral body. In another embodiment, the coupling member includes a distal portion extending into the vertebral body to engage the coupling member to a vertebral body. In other embodiments, various retaining members are provided to retain the longitudinal member to the coupling members.

Other embodiments include unique apparatus, devices, systems, and methods to stabilize vertebral bodies. Further embodiments, forms, objects, features, advantages, aspects, and benefits of the present application shall become apparent from the detailed description and figures included herewith.

DETAILED DESCRIPTION OF SELECTED EMBODIMENTS

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments and any further applications of the principles of the invention as described herein are contemplated as would normally occur to one skilled in the art to which the invention relates.

Figure 1:
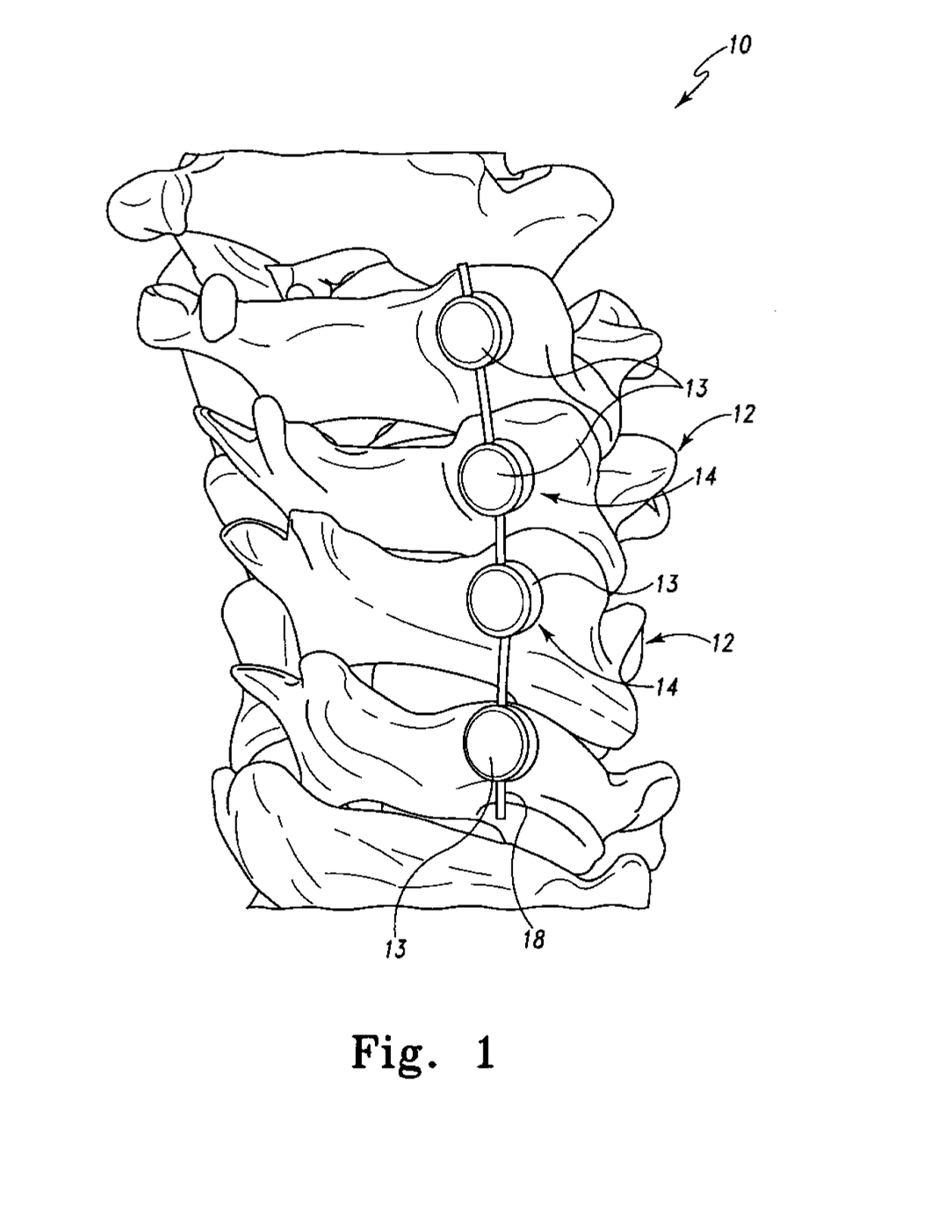
FIG. 1 is a perspective view of a spinal column segment with a vertebral stabilization system positioned thereon including a longitudinal member and coupling members shown diagrammatically.

FIG. 1 illustrates a spinal column segment 10 with a vertebral stabilization system 14 according to one aspect of the invention. Vertebral stabilization system 14 includes an elongated longitudinal member 18 extending along vertebrae 12 generally in the direction of the central axis of the spinal column segment 10. Vertebral stabilization system 14 also includes a number of coupling members 13 coupled to vertebrae 12 and longitudinal member 18 to secure longitudinal member 18 to the vertebrae 12. In one embodiment, coupling members 13 are configured to atraumatically engage the respective vertebrae 12 to maintain integrity of the bony tissue while providing a platform or base to which longitudinal member 18 can be mounted. In another embodiment, coupling members 13 provide a retaining device that is mounted thereto while allowing longitudinal member 18 to be positioned in engagement with the respective coupling member 13. The retaining device can than be manipulated to secure the longitudinal member 18 to the coupling member 13 without necessitating the surgeon to place or engage one or more separate components to the coupling member 13.

Longitudinal member 18 provides a desired stabilization effect to vertebrae 12 when secured thereto. Longitudinal member 18 can be in the form of a rod, wire, cable, tether, braid, suture, link, cord, plate, chain, or other device that is elongated to extend between at least two vertebrae 12. Longitudinal member 18 can be stiff, rigid, flexible, inflexible, formable, bendable, elastic, collapsible in compression and inelastic in tension, or otherwise movable in response to stimulus to provide a desired stabilization effect when coupled to vertebrae 12.

The vertebral stabilization system 14 can be secured to vertebrae 12 of the spinal column segment 10 from a posterior approach as shown. Also contemplated are procedures that involve in posterior-lateral, lateral, antero-lateral and anterior approaches to the spinal column. Stabilization system 14 can be secured to the anterior body portion of the vertebrae, or to any of the posterior elements of the vertebrae. The spinal column segment 10 may comprise two vertebrae 12 for a single level stabilization procedure or three or more vertebrae 12 in multi-level stabilization procedures. The vertebrae 12 can be any one or combination of the sacral, lumbar, thoracic, and cervical vertebrae of the spinal column. In addition, multiple longitudinal members can be secured to the vertebrae along the same vertebral levels or along different vertebral levels in the same procedure.

Referring now to FIG. 2A-2D, one embodiment of vertebral stabilization system 14 includes coupling member 13 with a base 16, longitudinal member 18, and a retaining member 20. Base 16 includes a distally oriented engagement surface 22, a proximally opening slot 24 located opposite engagement surface 22, and a passage 26 extending and opening proximally from engagement surface 22 with a plurality of threads 38 located therein. As used herein, the terms distal, distally, proximal and proximally are employed relative to the contemplated implantation orientation of vertebral stabilization system 14 along the spinal column. The terms distal and distally refer to the direction toward the patient and the terms proximal and proximally refer to the direction toward the surgeon and away from the patient. Longitudinal member extends from the respective coupling members 13 transversely to the distal-proximal direction for positioning along the spinal column.

Engagement surface 22 is configured to engage one or more bony surfaces of the respective vertebrae 12. In the illustrated embodiment, engagement surface 22 defines a through-hole 23 in communication with passage 26. Engagement surface 22 extends around through-hole 23 in a concentric circular arrangement. Engagement surface 22 can be smooth, or can be textured to enhance bonding of the adhesive to engagement surface 22. In another embodiment, engagement surface 22 is concavely curved to form a recess or depression in the distally oriented engagement surface 22. In other embodiments engagement surface 22 may be convexly curved, flat, angled, or include complex curvatures.

Figure 2A:
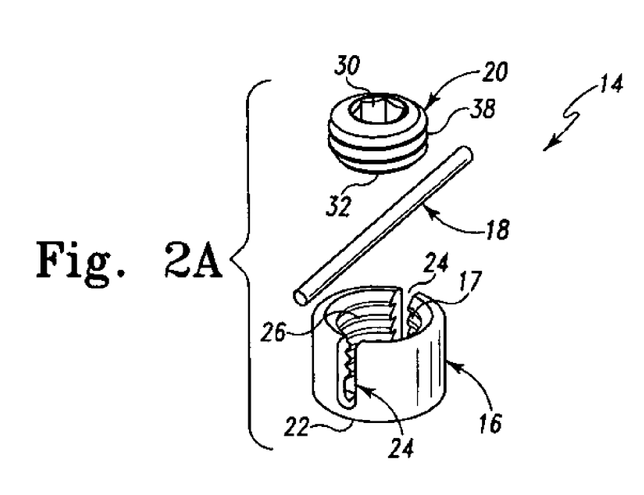
FIG. 2A is an exploded perspective of the vertebral stabilization system according to one embodiment.
Figure 2B:
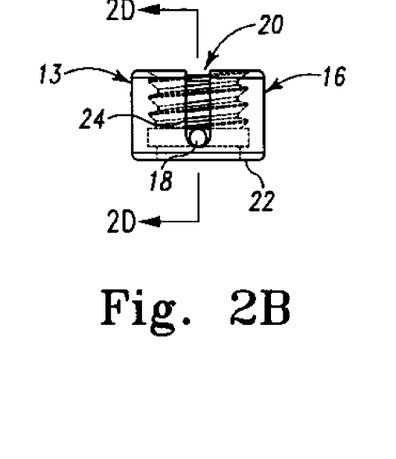
FIG. 2B is a side view of the vertebral stabilization system of FIG. 2A looking toward an end of the longitudinal member.
Figure 2C:
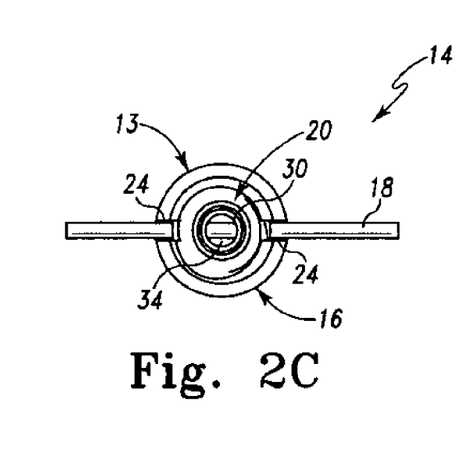
FIG. 2C is a top view of the vertebral stabilization system of FIG. 2A.

In one embodiment, base 16 is generally adhesively secured to the vertebra 12 by applying any suitable biocompatible adhesive between engagement surface 22 and the bony surface to be engaged. The adhesive sets to firmly engage base 16 to the bone surface of the respective vertebral body without requiring the trauma created by penetration of the vertebral body with a bone penetrating fastener such as a screw, staple or spike. Such atraumatic engagement substantially preserves the integrity of the bony tissue and simplifies attachment of the base 16 since no drilling or tapping is required to accommodate any fastener. In one procedure, the base 16 is atraumatically engaged to the bone surface of the vertebra without any preparation of the vertebra. In other procedures, tissue material can be removed from the bone surface to provide intimate contact between the engagement surface and the bone for atraumatic engagement of the engagement surface with the bone. For example, a limited amount of bone or tissue material can be scraped, chiseled or otherwise removed from the vertebra to form a receiving area in or adjacent to the bone surface to accommodate the engagement surface 22 and provide an intimate fit therewith. The bone surface can also be textured to enhance bonding of the adhesive thereto.

In other embodiments, base 16 may be secured to the vertebra 12 with an engagement surface 22 defining a suitable fastener arrangement that traumatically engages the bony tissue of the vertebral body. Contemplated fastener arrangements include bone screws, pins, wires, sutures, tacks, and staples, to name a few. In still other embodiments, one or more fastener arrangements are employed in combination with an adhesive.

Figure 2D:
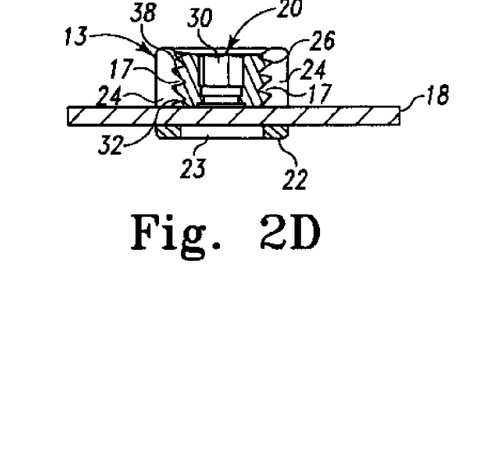
FIG. 2D is a section view of the vertebral stabilization system of FIG. 2A along line 2D-2D.

Slots 24 pass through the center of base 16 and extend distally from the proximal end of base 16 through its center to a location adjacent to engagement surface 22. In other embodiments slots 24 may not pass through the center of base 16. Slots 24 define a U-shape that opens along one of the respective opposite sides of base 16. Base 16 includes internal threads 17 formed therealong that extend about the inner surface thereof defined by passage 26. Internal threads 17 extend between the opposite slots 24. Slots 24 are sized to accommodate the size and shape of longitudinal member 18 in close fit with one another.

Retaining member 20 includes an outer thread profile 38, an instrument engaging portion 30, and a distally oriented longitudinal member engaging surface 32. The instrument engaging portion 30 is a hexagonally shaped recess, but may include other shapes to non-rotatably engage a driving instrument. In another form, engaging portion 30 is a stem about which a socket or wrench is positioned. Thread profile 38 is configured to engage the internal threads 17 in passage 26 of base 16. As the retaining member 20 is rotated with respect to the base 16, the distal longitudinal member engaging surface 32 urges the longitudinal member 18 against the bottom of the slots 24 to secure the longitudinal member 18 therewithin.

In use during one spinal stabilization procedure, the spinal column segment 10 is accessed from a desired approach for implantation of stabilization system 14. One base 16 is adhesively secured to one of the respective vertebrae 12, and the procedure is repeated for one or more additional vertebrae 12. Longitudinal member 18 is inserted into the slots 24 of each of the bases 16. Longitudinal member 18 may be bent, flexed or deformed for positioning into the slots 24 if so configured. Retaining members 20 are threadingly engaged into the passages of respective ones of the bases 16 to retain longitudinal member 18 in base 16. In one embodiment, retaining member 20 is positioned against longitudinal member 18 to urge it against the bottom of the slots 24 and fixedly engage longitudinal member 18 to base 16. In another embodiment, longitudinal member 18 is retained in slots 24 but permitted to float or axially translate in slots 24.

Referring now to FIGS. 3A-3D, another embodiment of vertebral stabilization system 14 is designated as system 114 and includes at least one coupling member 113 for securing longitudinal member 18 along the spinal column. Coupling member 113 includes a base 116 and a retaining member 120. Base 116 includes a distally oriented engagement surface 122 formed along a distal foot 121 and a post 125 extending proximally from foot 121. Post 125 includes a distal slot 124 located proximally of foot 121, and a passage 126 extending proximally from slot 124. Post 125 includes a thread profile 128 located on the outer surface thereof and a central opening 134 at the proximal end thereof that is in communication with passage 126.

Figures 3A, 3C:
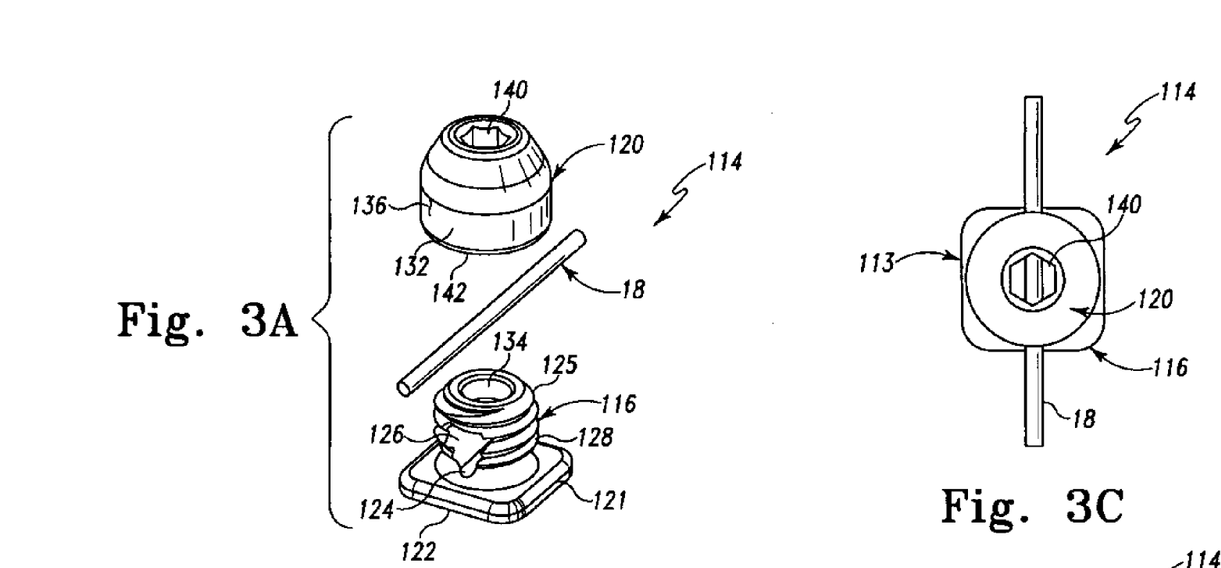
FIG. 3A is an exploded perspective of the vertebral stabilization system according to another embodiment.
FIG. 3C is a top view of the vertebral stabilization system of FIG. 3A.

Engagement surface 122 can receive an adhesive to secure it to a bone surface of the vertebra 12. Engagement surface 122 is flat in the illustrated embodiment and includes a square or rectangular footprint to increase the contact area with the bone surface. Other embodiments contemplate other configurations as discussed above with respect to engagement surface 22.

Slot 124 extends through post 125, and post 125 is solid around opening 134 between passage 126 and the proximal end of post 125 so that passage 126 is completely encircled by post 125. Slot 124 is located adjacent a distal end of post 125 adjacent foot 121. Passage 126 is enlarged relative to slot 124, and provides a distally tapered transition to slot 124 to facilitate centering of longitudinal member 18 into slot 124. The bottom of slot 124 is generally shaped to accommodate the size and shape of longitudinal member 18.

Retaining member 120 includes a cap 132 with a smooth, outer surface 136 that has a distal cylindrical portion and a proximally tapered frusto-conical shape extending from the distal cylindrical portion along with an internal thread profile 138. A proximal opening 140 is provided to receive a driving instrument. Other embodiments contemplate other arrangements for engaging a driving instrument as discussed above with respect to retaining member 20. Retaining member 120 also includes a distal longitudinal member engaging surface 142. Thread profile 138 is configured to threadingly engage thread profile 128 along post 125.

Figure 3B:
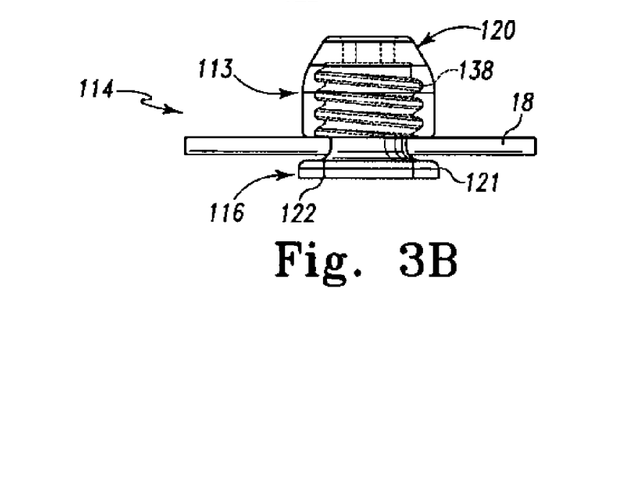
FIG. 3B is a side view of the vertebral stabilization system of FIG. 3A looking toward a length of the longitudinal member.
Figure 3D:
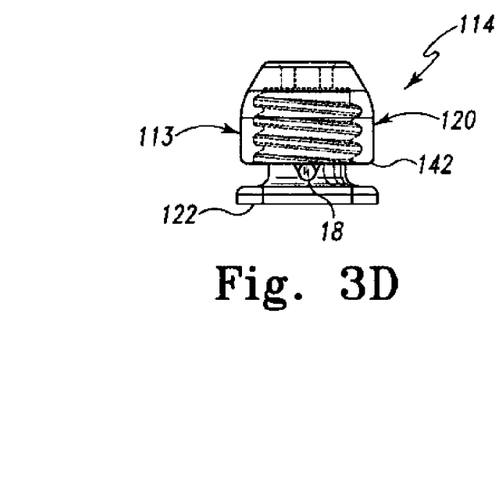
FIG. 3D is a side view of the vertebral stabilization system looking orthogonally to the direction of FIG. 3B.

Longitudinal member 18 is inserted in an end-wise manner through passage 126 of post 125 of each of the coupling members 113 of the stabilization system. Passage 126 can be elongated in the proximal and distal directions to facilitate placement of longitudinal member 18 therethrough. As retaining member 120 is rotated to engage post 125, longitudinal member engaging surface 142 contacts and urges longitudinal member 18 along passage 126 and into slot 124 against the bottom of slot 124 to secure longitudinal member 18 within slot 124 against foot 121. As shown in FIGS. 3B and 3D, longitudinal member 18 can be clamped at its contact locations with surface 142 to prevent any movement of longitudinal member 18 relative to coupling member 113. Two such clamped locations are provided where longitudinal member 18 exits slot 124 on opposite sides of post 125. Other embodiments contemplate arrangements between coupling member 113 and longitudinal member 18 where longitudinal member 18 is maintained, retained or restricted in coupling member 113 with retaining member 120.

Referring now to FIGS. 4A-4D, another embodiment of vertebral stabilization system 14 is designated as system 214. Stabilization system 214 includes at least one coupling member 213 for securing longitudinal member 18 along the spinal column. Coupling member 213 includes a base 216 and, like coupling member 13 discussed above, retaining member 20. Base 216 includes a distal foot 221 having a distal engagement surface 222. A post 225 extends proximally from foot 221, and includes a pair of semi-cylindrical arms 227, 229 that form a proximally opening passage 226 therebetween. Arms 227, 229 are spaced from one another with opposite slots 224. Slots 224 can be tapered distally so that a distal end thereof adjacent foot 221 is sized and shaped to receive longitudinal member 18 in a close fit while the proximal portions of slots 224 are enlarged to facilitate placement of longitudinal member 18 into slots 224.

Figure 4A:
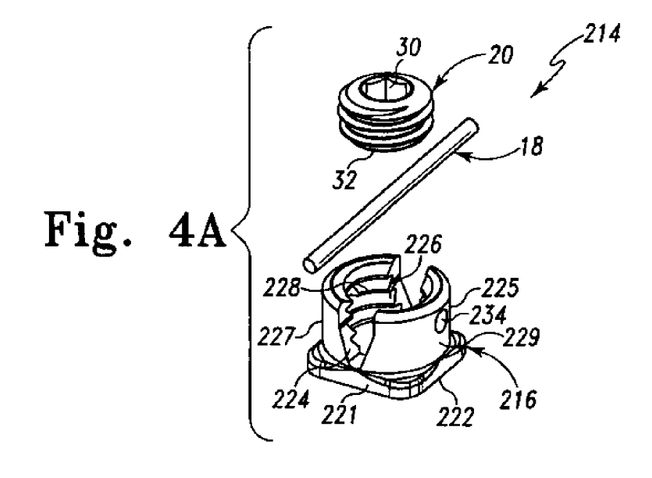
FIG. 4A is an exploded perspective of the vertebral stabilization system according to yet another embodiment.
Figure 4B:
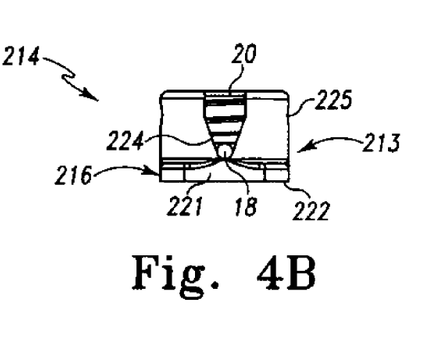
FIG. 4B is a side view of the vertebral stabilization system of FIG. 4A looking toward an end of the longitudinal member.
Figure 4C:
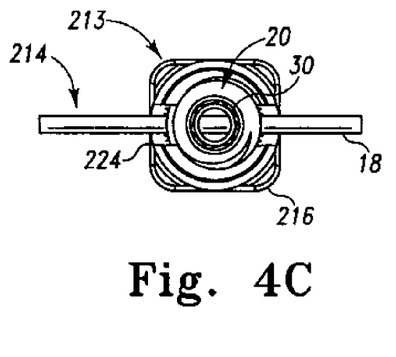
FIG. 4C is a top view of the vertebral stabilization system of FIG. 4A.
Figure 4D:
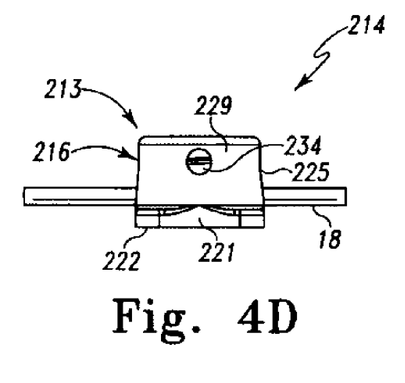
FIG. 4D is a side view of the vertebral stabilization system looking orthogonally to the direction of FIG. 4B.

Engagement surface 222 can receive an adhesive to secure it to a bone surface of the vertebra 12. Engagement surface 222 is flat in the illustrated embodiment and includes a square or rectangular footprint to increase the contact area with the bone surface. Other embodiments contemplate other configurations as discussed above with respect to engagement surface 22.

Arms 227, 229 include a thread profile 228 in the concavely curved side thereof that extends along passage 226. Arms 227, 229 also include transverse receptacles 234 to receive a portion of an insertion and placement instrument, facilitating the grasping of base 216 with such instruments so it can be positioned into the patient during surgery. When longitudinal member 18 is positioned in passage 226, retaining member 20 is engaged into the proximal opening of passage 226 to arms 227, 229. Retaining member 20 is threaded along arms 227, 229 to move longitudinal member 18 distally along slots 224 to seat in the distal end thereof adjacent foot 221. Retaining member 20 can apply sufficient torque to clamp longitudinal member 18 at the sides of retaining member 20 opposite of instrument engaging portion 30. Other embodiments contemplate non-clamped engagement of longitudinal member 18 in coupling member 213.

Referring now to FIGS. 5A-5D, another embodiment of vertebral stabilization system 14 is designated as system 314. System 314 includes at least one coupling member 313 and longitudinal member 18. Coupling member 313 includes a base 316 and a retaining member 320 that is positionable about and rotatable relative to base 316.

Figure 5A:
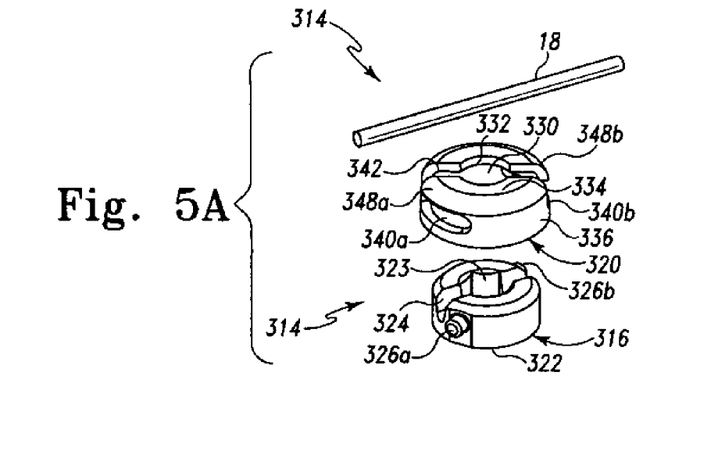
FIG. 5A is an exploded perspective of the vertebral stabilization system according to another embodiment.
Figure 5B:
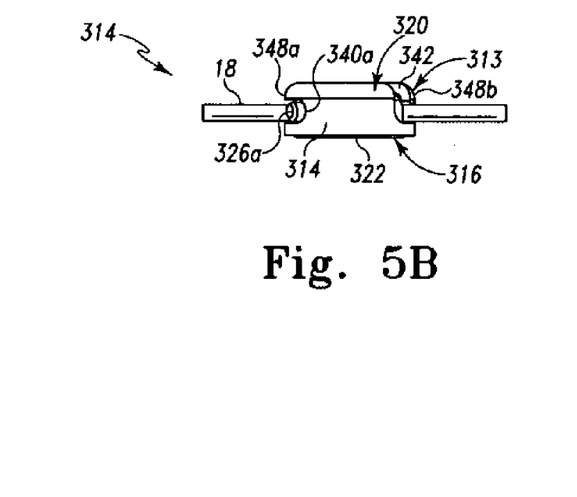
FIG. 5B is a side view of the vertebral stabilization system of FIG. 5A looking toward a length of the longitudinal member.

Base 316 includes a distal engagement surface 322 that is securable to the bone surface of the vertebra 12 with an adhesive. Engagement surface 322 is flat and circular in shape in the illustrated embodiment. Other embodiments contemplate other shapes and forms for engagement surface 322 as discussed above with respect to engagement surface 22.

Base 316 includes a distal slot 324 extending therein from the proximal side thereof. Slot 324 includes an enlarged central portion 323. Base 316 further includes opposite outwardly extending engaging members 326a, 326b that are in the form of cylindrical pins in the illustrated embodiment.

Retaining member 320 is in the form of a cylindrical disc with a distally opening passage 330 that is sized to extend around the outer perimeter of base 316. Retaining member 320 includes proximal opening 332 formed in proximal end wall 334 and sidewall 336 extending distally from end wall 334 around passage 330. Retaining member 320 also includes a proximal slot 342 extending across proximal end wall 334 and into sidewall 336. Transverse slots 340a and 340b extend from respective ends of proximal slot 342 around a portion of the perimeter of sidewall 336. Transverse slots 340a, 340b and proximal slot 342 divide sidewall 336 to form opposite fingers 348a, 348b extending along slots 340a, 340b, respectively. Proximal opening 332 can facilitate placement of an instrument to engage longitudinal member 18 in slot 324, or to receive a bead or other structure extending about longitudinal member 18. Proximal opening 332 can receive an instrument that rotates retaining member 320 to secure it to base 316. Proximal opening 332 can also provide an arrangement with slots 342 that allows a counter-torque to be engaged to base 316 while an instrument in slots 342 rotates retaining member 320.

Figure 5C:
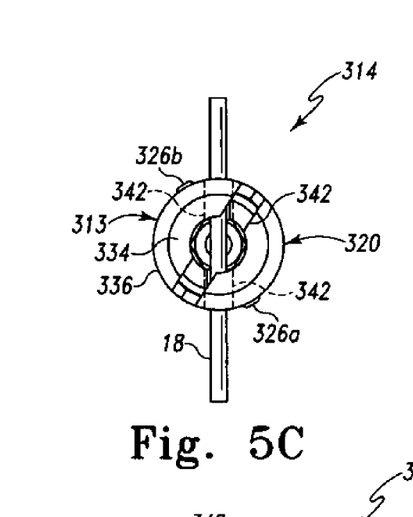
FIG. 5C is a top view of the vertebral stabilization system of FIG. 5A.

With retaining member 320 assembled to base 316, coupling member 313 is secured to the vertebral body. Retaining member 320 is positioned on base 316 in a first orientation so that proximal slot 342 of retaining member 320 is aligned with distal slot 324 of base 316, as indicated by the dashed lines of FIG. 5C. In this orientation, engaging members 326a, 326b are located in transverse slots 340a, 340b) adjacent proximal slot 342. Longitudinal member 18 can be positioned through proximal slot 342 and into distal slot 324 until aligned or generally aligned with transverse slots 340a, 340b. Retaining member 320 is then rotated to a second orientation where engaging members 326a, 326b are located adjacent the ends of slots 340a, 340b remote from proximal slot 342. In the second orientation, longitudinal member 18 is located in transverse slots 340a, 340b and proximal slot 342 extends obliquely to longitudinal member 318, as best shown in FIG. 5C. In the second orientation, fingers 348a, 348b of sidewall 336 capture longitudinal member 18 in slot 324, and engaging members 326a, 326b engage sidewall 336 to prevent retaining member 320 from being removed from base 316.

Figure 5D:
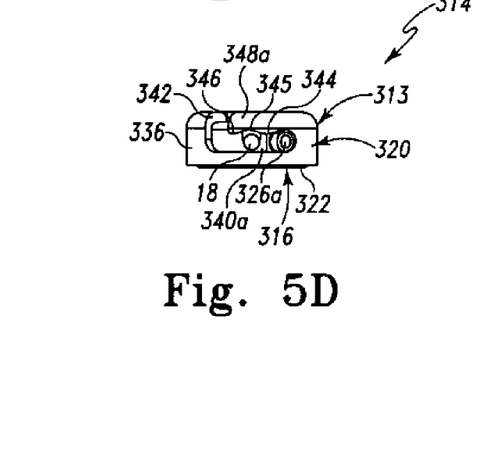
FIG. 5D is a side view of the vertebral stabilization system looking orthogonally to the direction of FIG. 5B.

As best shown in FIG. 5D, sidewall 336 includes a projection 344 along and extending into each of the transverse slots 340a, 340b from the respective finger 348a, 248b. The projection maintains retaining member 320 in the second orientation to prevent it from rotating relative to base 316 and secured the respective engaging member 326a, 326b adjacent the blind end of the respective transverse slot 340a, 340b. Fingers 348a, 348b can flex above the respective adjacent transverse slot 340a, 340b to allow passage, if needed, of the projection 344 over longitudinal member 18 upon application of sufficient force. Fingers 348a, 348b of sidewall 336 also include a second projection 346 adjacent proximal slot 342 to form a recess 345 to receive the respective adjacent engaging member 326a, 326b and maintain retaining member 320 in the first orientation relative to base 316.

In the second orientation, longitudinal member 18 is positioned in transverse slots 340a, 340b and is captured therein by fingers 348a, 348b of sidewall 336. Longitudinal member 18 is spaced from sidewall 336 in slots 340a, 340b so that longitudinal member 18 can move at least longitudinally relative to coupling member 313. In this condition, spinal motion of the stabilized vertebral levels remains is permitted, but is restrained in rotation and lateral extension by tensioning of longitudinal member 18. Other arrangements contemplate an engagement relationship where longitudinal member 18 is constrained relative to coupling member 313. For example, sidewall 336 can contact longitudinal member 18 to restrict longitudinal movement of longitudinal member 18 relative to coupling member 313. In other forms, a set screw, crimp or other device can be engaged to or in retaining member 320 and with longitudinal member 18 to secure it within base 316.

Figure 6:
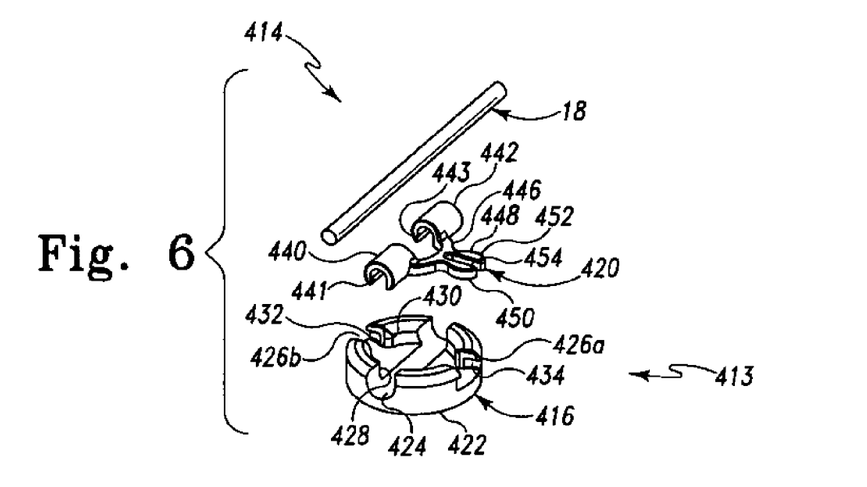
FIG. 6 is an exploded perspective of the vertebral stabilization system according to still another embodiment.

Referring now to FIG. 6, another embodiment of stabilization system 14 is shown and designated as stabilization system 414 with a coupling member 413 and longitudinal member 18. Coupling member 413 includes a base 416 and a retaining member 420. Base 416 includes a cylindrical disc shape with a distal engagement surface 422 and a proximally oriented slot 424 opposite engagement surface 422. Distal engagement surface 422 is securable to the bone surface of the vertebra 12 with an adhesive. Engagement surface 422 is flat and circular in shape in the illustrated embodiment. Other embodiments contemplate other shapes and forms for engagement surface 422 as discussed above with respect to engagement surface 22.

The proximal side of base 416 includes engagement recesses 426a, 426b on opposite sides thereof that are in communication with slot 424. Each engagement recess 426a, 426b includes an enlarged portion 428 having a semi-circular shape adjacent slot 424 and an outer portion 432 adjacent the outer perimeter of base 416. Outer portion 432 includes a grooved portion 434 extending thereabout. Outer portion 432 is connected to enlarged portion 428 with a neck portion 430.

Retaining member 420 is engageable to longitudinal member 18 and to base 416 to secure longitudinal member 18 to base 416. Retaining member 420 includes receiving portions 440, 442 that have a semi-cylindrical shape and form a receiving passage 441, 443, respectively, to receive longitudinal member 18 therein. Receiving portions 440, 442 are linked by a connecting arm 446 having a semi-circular shape. An engaging member 448 extends from connecting arm 446 opposite receiving portions 440, 442. Engaging member 448 includes a pair of legs 450, 452 separated by a central slot 454. Slot 454 allows legs 450, 452 to resiliently flex toward one another in response to compression forces moving the legs 450, 452 toward one another.

Figure 7A:
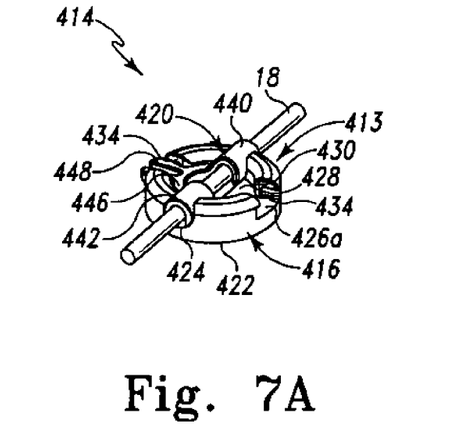
FIG. 7A is a perspective view of the vertebral stabilization system of FIG. 6 in a first orientation.
Figure 7B:
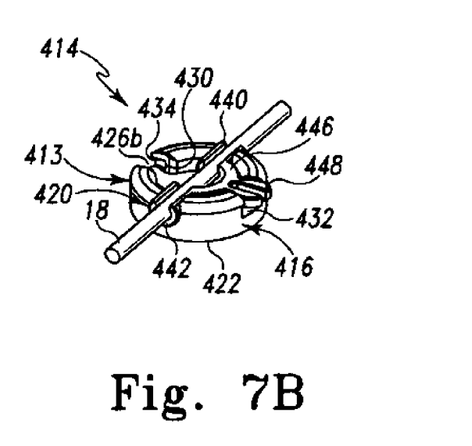
FIG. 7B is a perspective view of the vertebral stabilization system of FIG. 6 in a second orientation.

FIGS. 7A and 7B show retaining member 420 configured to secure longitudinal member 18 to base 416. In FIG. 7A retaining member 420 is positioned with engaging member 448 in outer portion 432 of engagement recess 426b. Legs 450, 452 are slightly compressed toward one another and reside in grooved portion 434 to secure retaining member 420 to base 416. Engaging member 448 extends through neck portion 430 and connecting arm 446 is located in enlarged portion 428 of engagement recess 426b. Receiving portions 440, 442 are oriented so that receiving passages 441, 443 are oriented distally in slot 424 of base 416 and positioned around longitudinal member 18. Receiving portions 440, 442 frictionally engage the sides of slot 424 to resist displacement of receiving portions 440, 442 from slot 424. Retaining member 420 captures longitudinal member 18 in slot 424 and maintains it in engagement with base 416. In one procedure, longitudinal member 18 is positioned in or adjacent slot 424, and retaining member 420 is positioned so that receiving portions 440, 442 are located around longitudinal member 18 and engaging member 448 engages engagement recess 426b. Receiving portions 440, 442 are, if necessary, then positioned into slot 424. Alternatively, retaining member 420 can be oriented to engage base 416 in engagement recess 426a with passages 441, 443 opening distally into slot 424.

FIG. 7B is similar to FIG. 7A except retaining member 420 is positioned with passages 441, 443 of receiving portions 440, 442 oriented proximally and engaging member 448 is secured in engagement recess 426a. In this configuration, longitudinal member 18 can be press fit into receiving portions 440, 442 either before or after retaining member 420 is engaged to base 416. Alternatively, retaining member 420 can be oriented to engage base 416 in engagement recess 426b with receiving portions 440, 442 oriented to open passages 441, 443 proximally in slot 424. In either orientation, longitudinal member 18 is configured to be press fit into receiving portions 440, 442 to maintain it in engagement with base 416.

In another procedure, base 416 of coupling member 413 is secured to the bony surface of a vertebra. Retaining member 420 is secured to base 416 in the orientation of FIG. 7B either before or after engagement of base 416 to the vertebra. Longitudinal member 18 is positioned into the proximally opening receiving portions 440, 442. Retaining member 420 is then released from engagement recess 426a and rotated to the position of FIG. 7A so that engaging member 448 engages engagement recess 426b and receiving portions 440, 442 are oriented so that passages 441, 443 open distally toward base 416. Longitudinal member 18 is captured between base 416 and retaining member 420. Receiving portions 440, 442 can frictionally engage longitudinal member 18 to prevent or restrict longitudinal movement of member 18 relative to base 416. In another embodiment, longitudinal member 18 is sized relative to receiving passages 441, 443 to allow longitudinal movement longitudinal member 18 relative to coupling member 413.

Referring now to FIGS. 8A-8D, another embodiment of vertebral stabilization system 14 is designated as stabilization system 514. Stabilization system 514 includes a coupling member 513 and longitudinal member 18 secured to coupling member 513 to provide stabilization along a spinal column segment when coupling member 513 is secured to a vertebra. Coupling member 513 includes retaining element 420 like that discussed above with respect to FIGS. 6 and 7A-7B. Coupling member 513 also includes base 516 that has a base portion 522 and a saddle portion 540. Saddle portion 540 includes a mounting member 542 that is pivotally mounted to base portion 522 to allow pivoting movement of saddle portion 540 relative to base portion 522.

Figure 8A:
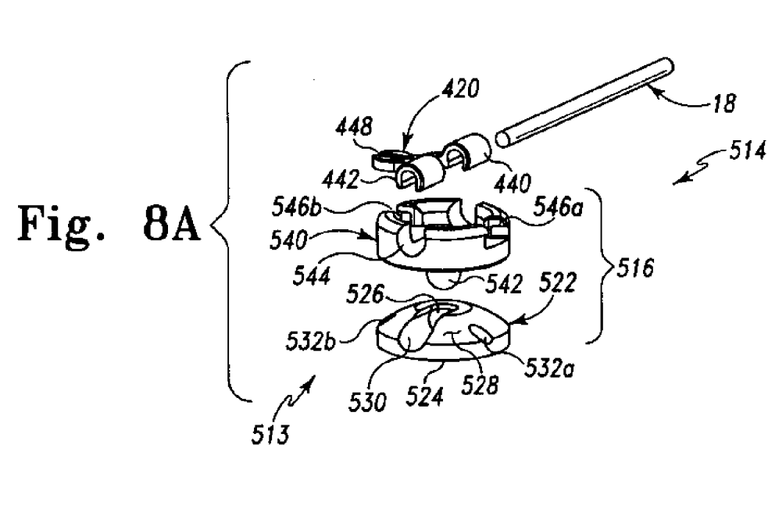
FIG. 8A is an exploded perspective of the vertebral stabilization system according to still another embodiment.
Figure 8B:
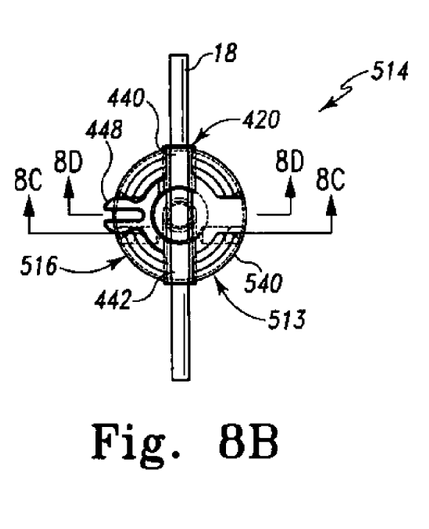
FIG. 8B is a top view of the vertebral stabilization system of FIG. 8A.

Saddle portion 540 is similar to base 416 discussed above, but includes mounting member 542 extending distally therefrom rather than a distal engagement surface. Otherwise, saddle portion 540 includes a proximally oriented slot 544 to receive longitudinal member 18, and opposite engaging recesses 546a, 546b to receiving retaining element 420 in the manner discussed above with respect to base 416 of coupling member 413.

Base portion 522 includes a distally oriented engagement surface 524 that is positionable in contact with the bony surface of a vertebral body. Engagement surface 524 can be secured with an adhesive to the bony surface as discussed above with respect to engagement surface 22. Other embodiments contemplate other forms for engagement surface 524 as discussed above with respect to engagement surface 22.

Figure 8C:
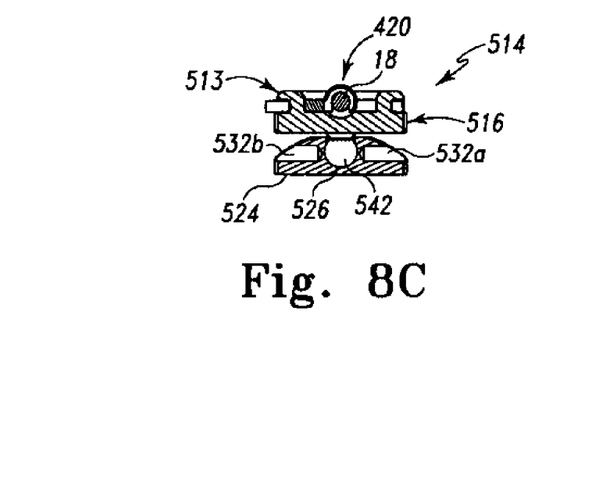
FIG. 8C is a cross-sectional view of the vertebral stabilization system of FIG. 8A along line 8C-8C of FIG. 8B.

Base portion 522 further includes a proximally opening socket 526 centered therein in a dome-shaped proximal surface 528. Base portion 522 further includes a side-opening lead-in passage 530 in surface 528 that is in communication with socket 526. Deformation passages 532a, 532b extend orthogonally to lead-in passage 530 and include blind ends adjacent thereto at a location offset from socket 526, as best shown in FIG. 8C.

Figure 8D:
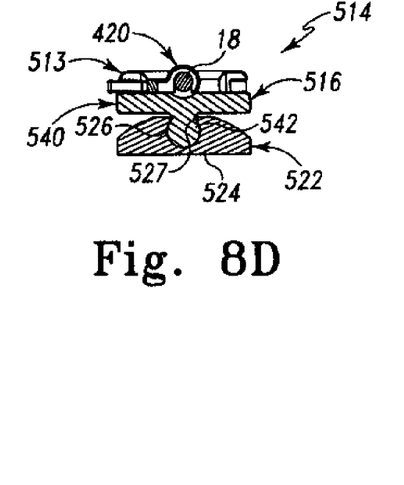
FIG. 8D is a cross-sectional view of the vertebral stabilization system of FIG. 8A along line 8D-8D of FIG. 8B.

Saddle portion 540 is assembled with base portion 522 by positioning mounting member 542 in lead-in passage 530 and moving mounting member therealong and into socket 526. Mounting member 542 includes a spherical shape and is axially restrained in socket 526 at neck portion 527 of socket 526 as best shown in FIG. 8D. To prevent mounting member 542 from displacing back through lead-in passage 530, base portion 522 can be deformed by placing pliers, forceps or other squeezing type instrument in deformation passages 532a, 532b and deforming the material of base portion 522 to reduce the size of at least a portion of lead-in passage 530 to retain mounting member 542 in socket 526. Mounting member 542 retains its pivotal movement capability in socket 526 so that saddle portion 540 is pivotal relative to base portion 522.

Figure 9:
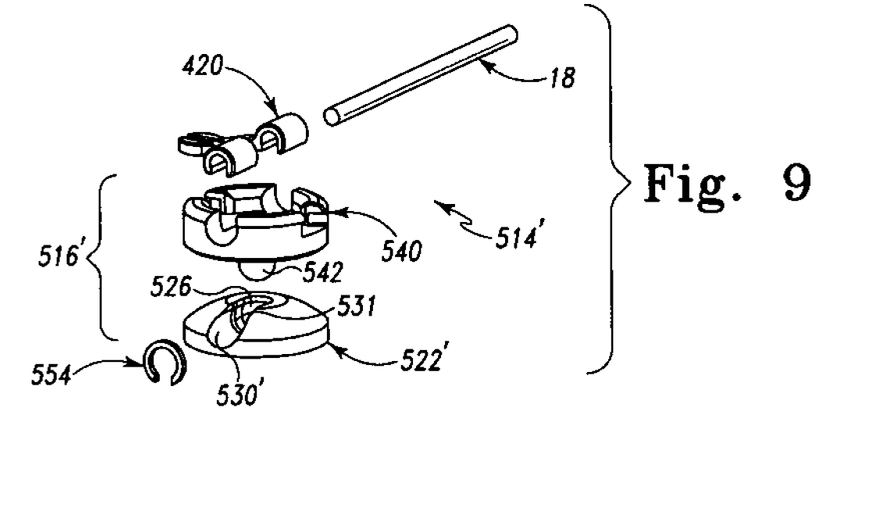
FIG. 9 is an exploded perspective view of the vertebral stabilization system of FIG. 8A utilizing a retaining clip.

In another embodiment shown in FIG. 9, stabilization system 514' is similar to stabilization system 514, but includes an alternate means for securing mounting member 542 in socket 526. Base portion 522' of base 516' does not include deformation passages, although providing the same is not precluded. Base portion 522' includes a lead-in passage 530' that includes a groove 531 formed therein to receiving a retention member 554. Retention member 554 is in the form of a C-shaped clip that is positioned in groove 531 to block lead-in passage 530' at socket 526, and prevent mounting member 542 from backing out of socket 526 after insertion therein from lead-in passage 530'.

In either of the embodiments for stabilization systems 514 and 514' the saddle portion is pivotal relative to the base portion so that the base to which the longitudinal member is coupled can pivot to permit at least some range of spinal motion while providing stabilization and limitations to the spinal motion of the stabilized vertebral levels. The pivoting arrangement of the saddle portion relative to the base portion can also facilitate assembly of the spinal stabilization system since coupling members can be manipulated to align the receiving slot in a desired orientation suited to receive the longitudinal member. It is contemplated that stabilization systems can be assembled that include multiple coupling members 513, 513' having pivoting capabilities, either alone or in combination with one or more of the other coupling members 13, 113, 213, 313, 413 disclosed herein that do not providing pivoting capability.

Figure 10:
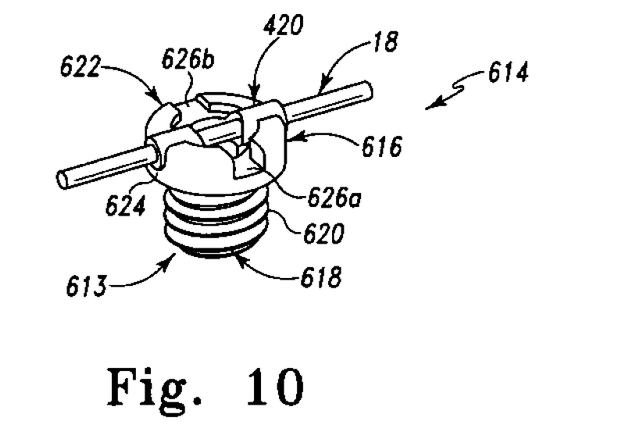
FIG. 10 is a perspective of the vertebral stabilization system according to still another embodiment.

Referring now to FIG. 10, there is shown another embodiment of vertebral stabilization system 14 designated as vertebral stabilization system 614. System 614 includes a coupling member 613 with a base 616 and retaining member 420 secured to base 616 to couple longitudinal member 18 to base 616. Base 616 includes a distal engagement portion 618 with a thread profile 620 extending therealong to threadingly engage a bony structure such as a vertebra 12. Base 616 also includes a proximal portion 622 that includes proximally extending slot 624 and engagement recesses 626a, 626b to engage retaining member 420. Proximal portion 622 can be configured like the proximally oriented portion of base 416 discussed above to secure retaining member 420 thereto.

In another embodiment, proximal portion 622 can be configured like base 316 discussed above and a retaining member like retaining member 320 is provided for engagement thereto. In another embodiment, proximal portion 622 can be configured like base 216 or base 16 discussed above and a retaining member like retaining member 20 is provided for engagement thereto. In yet another embodiment, proximal portion 622 can be configured like base 116 discussed above and a retaining member like retaining member 120 is provided for engagement thereto.

Figure 11A:
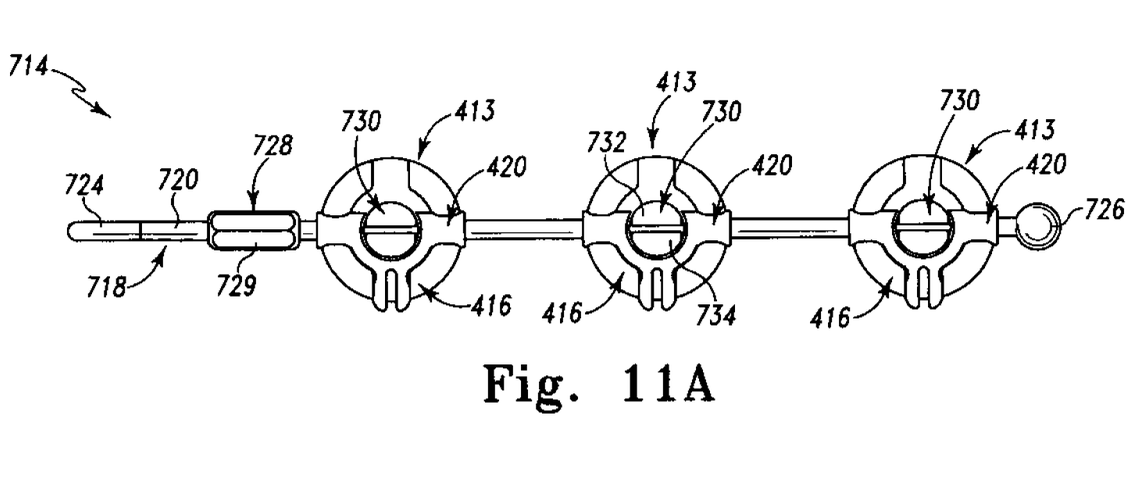
FIGS. 11A and 11B are a plan view and elevation view, respectively, of another embodiment stabilization system.
Figure 11B:
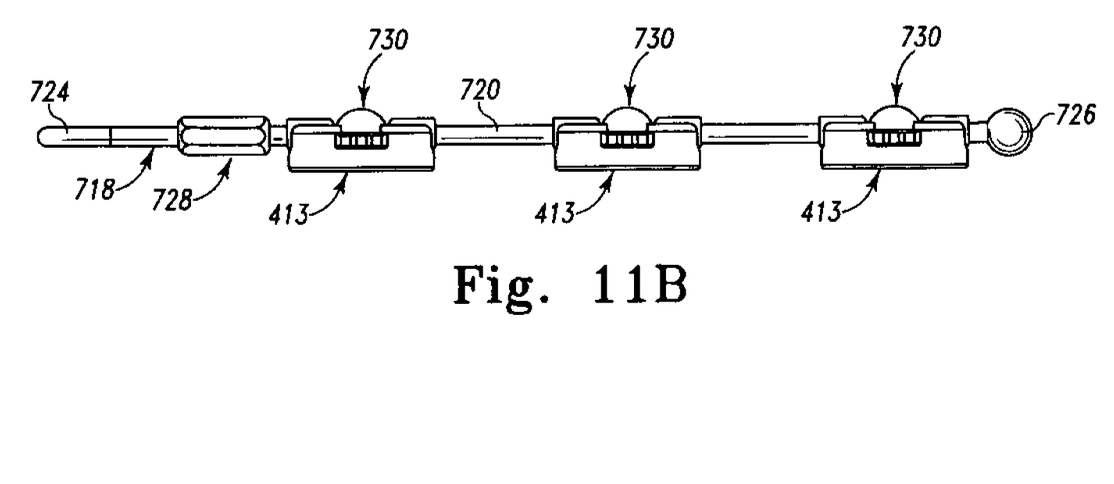

FIGS. 11A and 11B show another embodiment stabilization system 714 that includes a plurality of coupling members 413 spaced along another embodiment longitudinal member 718. Longitudinal member 718 includes a flexible portion 720 that is secured to bases 416 with the respective retaining members 420 as discussed above. Longitudinal member 718 also includes a rigid leader portion 724 at one end thereof to facilitate insertion of longitudinal member 718 through the bases, retaining members and/or crimps.

Stabilization system 714 further includes a plurality of internal crimps 730 that are securely engaged to longitudinal member 718 in the central space formed between receiving portions 440, 442 of the respective retaining members 420.

Internal crimps 730 include a central passage to receive longitudinal member 718 and opposite portions 732, 734 that are squeezed or crimped together to engage longitudinal member 718 in the central passage. Internal crimps 730 contact at least one of retaining member 420 and base 416 to prevent longitudinal member 718 from moving axially relative to the respective coupling member 413. While each of the coupling members 413 is shown with an internal crimp 730, it is contemplated that fewer than all the coupling members 413 or none of the coupling members 413 can be provided with an internal crimp 730.

In addition to or in lieu of internal crimps 730, longitudinal member 718 is provided with an external crimp 728 positioned therealong outside of and adjacent to one or both of the coupling members 413 at the opposite ends of longitudinal member 718. In other embodiments, external crimps 728 are positioned along longitudinal member 718 between coupling members 413. External crimp 728 includes a central passage to receive longitudinal member 728 and an outer wall 729 that is deformable to crimp or engage longitudinal member 718 in the passage. External crimp 728 can abut the adjacent coupling member 413 to maintain a tension or relative positioning the longitudinal member 718 relative to the coupling members 413. In lieu of an external crimp 728, one of the ends of longitudinal member 718 can be provided with an enlarged retaining portion 726 formed integrally or pre-attached therewith at the end of longitudinal member 718. Retaining portion 726 abuts or is positioned adjacent to the respective coupling member 413, and acts with the external crimp 728 to maintain compression or limit displacement of the vertebral levels along which longitudinal member 718 is engaged.

In one procedure, longitudinal member 718 is positioned along the coupling members 413 with retaining member 726 adjacent the most cephalad or most caudal coupling member 413, and external crimp 728 is moved along longitudinal member 718 to a location adjacent the other of the most cephalad and caudal coupling members 413. When the desired tension and positioning of longitudinal member 718 has been achieved, external crimp 728 is engaged to longitudinal member 718 to maintain the tension and positioning of longitudinal member 718 relative to the coupling members 413. Alternatively or additionally, internal crimps 730 can be engaged to longitudinal member 718 in the respective coupling members 413 to maintain the axial positioning and tensioning of longitudinal member 718 relative to the respective coupling member 413. In still other embodiments, longitudinal member 718 and crimps 728, 730 are employed with any one or combination of the coupling member embodiments discussed herein.

Crimps 728, 730 can be engaged to longitudinal member 718 prior to delivery of longitudinal member 718 to the implantation location. In other embodiments, internal crimps 730 are not engage tightly to longitudinal member 718, and are allowed to translate along longitudinal member 718 in response to spinal motion. Longitudinal member 718 can work in conjunction with the coupling members to provide a tension bands to allow vertebral load sharing but restrict motion by tensioning to limit vertebral displacement.

The stabilization systems can employ a number of identical coupling members to secure the longitudinal member 18 to the vertebrae 12. Other embodiments contemplate systems employing various combinations of types of coupling members. For example, the coupling members at the cephalad and caudal ends of the longitudinal member can be configured to crimp or otherwise fixedly retain the longitudinal, member therein, while one or more intermediate coupling members can be configured to permit axial translation of the longitudinal member, or to provide a pivoting platform to which the longitudinal member is engaged.

The longitudinal member can be rigid such as with a metal spinal rod or flexible like a cable or tether. The longitudinal member can be made from any suitable biocompatible material, including titanium and titanium alloys, nickel-titanium alloys, superelastic materials, shape memory materials, stainless steel and stainless steel alloys, polymers or polymeric material such as polyetheretherketone, fabrics, polyesters, or elastomers, for example. The longitudinal member can include any cross-sectional profile, including round, oval, square, rectangular, polygonal or irregular cross-sections. The longitudinal member can provide stiffness to resist axial compression loading, or can be collapsible under compression loading resulting from spinal loads. The longitudinal member can be tensioned and then secured between respective ones of the coupling members so that when the tension is released the longitudinal member is pre-stressed to apply a compression loading between the stabilized vertebral level or levels. The longitudinal members can be provided in pre-set lengths, or can be cut to a desired length before or after implantation.

Any theory, mechanism of operation, proof, or finding stated herein is meant to further enhance understanding of the present invention and is not intended to make the present invention in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the invention, that scope being defined by the claims that follow. In reading the claims it is intended that when words such as "a," "an," "at least one," "at least a portion" are used there is no intention to limit the claim to only one item unless specifically stated to the contrary in the claim. Further, when the language "at least a portion" and/or "a portion" is used the item may include a portion and/or the entire item unless specifically stated to the contrary. While the invention has been illustrated and described in detail in the drawings and foregoing description, the same is to be considered as illustrative and not restrictive in character, it being understood that only the selected embodiments have been shown and described and that all changes, modifications and equivalents that come within the spirit of the invention as defined herein or by any of the following claims are desired to be protected.

What is claimed is:

1. A method for spinal stabilization, comprising:
    providing a plurality of coupling members each having an outer surface that is free of threads;
    adhesively securing the plurality of coupling members to respective ones of a plurality of vertebrae;
    positioning a longitudinal member between the plurality of coupling members; and
    securing the longitudinal member to the plurality of coupling members;
    wherein the coupling members each include a cavity, the longitudinal member includes a crimp, and securing the longitudinal member includes:
        positioning an enlarged retaining end of the longitudinal member adjacent one of the plurality of coupling members that is secured to a most cephalad or most caudal vertebral body; and
        positioning the crimp in one of the cavities.

2. The method of claim 1, wherein securing the longitudinal member includes threadingly engaging a retaining member between a pair of arms of at least one of the coupling members to secure the longitudinal member in a base of the coupling member.

3. The method of claim 1, wherein:
the coupling member includes a distal base with a distal engagement surface applied with adhesive and a proximal retaining member;
positioning the longitudinal member includes positioning the longitudinal member into aligned slots of the retaining member and the base; and
securing the longitudinal member includes rotating the retaining member around the base to position the longitudinal member in opposite transverse slots in a sidewall of the retaining member.

4. The method of claim 3, wherein the base includes outwardly extending engaging members received in respective ones of the transverse slots of the retaining member to secure the retaining member to the base.

5. The method of claim 4, wherein the sidewall includes a finger portion extending along respective ones of the transverse slots, the finger portions each including at least one projection extending into the respective adjacent transverse slot, the at least one projection engaging the engaging member positioned in the respective slot to resist rotation of the retaining member relative to the base.

6. The method of claim 1, wherein:
the coupling member includes a distal base with a distal engagement surface applied with adhesive and a proximal retaining member;
positioning the longitudinal member includes positioning the longitudinal member into a passage of the retaining member; and
securing the longitudinal member includes pivoting the retaining member around the longitudinal member and relative to the base to secure the retaining member to the base with the passage of the retaining member oriented toward a slot of the base.

7. The method of claim 1, wherein the longitudinal member is a cord-like member that collapses in response to axial compression loading and is inelastic in tension, and further comprising tensioning the longitudinal member after positioning the longitudinal member.

8. The method of claim 1, further comprising bending the longitudinal member while positioning the longitudinal member between the plurality of coupling members.

9. The method of claim 1, further comprising engaging the crimp around the longitudinal member at an end of the longitudinal member opposite the enlarged retaining end.

10. The method of claim 9, wherein:
the crimp comprises a central passage defined by opposite portions of the crimp; and
engaging the crimp includes squeezing or crimping the opposite portions of the crimp together to engage the longitudinal member in the central passage.

11. The method of claim 9, wherein engaging the crimp occurs prior to positioning the longitudinal member.

12. The method of claim 1, further comprising texturing at least one of the vertebrae to enhance bonding of adhesive thereto.

13. The method of claim 1, further comprising removing tissue material from one of the vertebrae to form a receiving area to accommodate one of the coupling members.

14. A method for spinal stabilization, comprising:
providing a plurality of coupling members each including a plate having an engaging surface applied with adhesive and an opposite first surface including a post extending proximally therefrom, the post including a passage extending parallel to the first surface, the passage tapering into a slot, the passage being spaced apart from a proximal end surface of the post;
adhesively securing the plurality of coupling members to respective ones of a plurality of vertebrae;
positioning a longitudinal member through the passages; and
securing the longitudinal member to the plurality of coupling members by mating threads of a respective retaining member with threads on an outer surface of each post such that a distal end surface of each retaining member engages said longitudinal member to position said longitudinal member into said slot.

15. The method of claim 14, wherein the posts each include a central opening extending through the proximal end surface that is in communication with the passage, the central opening terminating prior to the plate.

16. The method of claim 14, wherein the coupling members each include a neck positioned between the plate and the post that includes an outer surface that is free of threads, the neck having a maximum diameter that is less than a maximum diameter of the post, the slot extending through the neck.

17. A method for spinal stabilization, comprising:
providing a plurality of coupling members each including a base portion having a semispherical socket and a saddle portion having a substantially spherical extension disposed in the socket to pivotally couple the saddle portion to the base portion;
adhesively securing the plurality of coupling members to respective ones of a plurality of vertebrae;
positioning a longitudinal member through a passage in a retaining member; and
securing the longitudinal member to the plurality of coupling members by disposing an engaging member of each retaining member in a first slot in each saddle portion.

18. The method of claim 17, wherein the saddle portions each include a second slot extending perpendicular to the first slot, the longitudinal member being positioned in the second slot when the engaging member is disposed in the first slot.

19. The method of claim 17, wherein:
the engaging members each have a maximum width that is greater than a maximum width of the first slot; and
securing the longitudinal members includes deforming the engaging members prior to disposing the engaging members in the first slots.

* * * * *